United States Patent
Blunsden

[19]

[11] Patent Number: 6,104,954
[45] Date of Patent: Aug. 15, 2000

[54] HIGH FREQUENCY LEAD TESTING APPARATUS IN AN IMPLANTABLE DEFIBRILLATOR

[76] Inventor: Christopher K. Blunsden, 14 Palm Rd, Newport Beach, Australia, 2106

[21] Appl. No.: 08/886,049

[22] Filed: Jun. 30, 1997

[51] Int. Cl.[7] .................................................. A61N 1/39
[52] U.S. Cl. ............................................................ 607/8
[58] Field of Search .................................... 607/4, 5, 8

[56] References Cited

U.S. PATENT DOCUMENTS

| | | | |
|---|---|---|---|
| 5,083,562 | 1/1992 | De Coriolis et al. | 607/7 |
| 5,201,865 | 4/1993 | Kuehn | 607/8 |
| 5,215,081 | 6/1993 | Ostroff | 607/8 |
| 5,215,083 | 6/1993 | Drane et al. | 607/4 |
| 5,330,504 | 7/1994 | Somerville et al. | 607/5 |
| 5,755,742 | 5/1998 | Schuelke et al. | 607/27 |

*Primary Examiner*—Jeffrey R. Jastrzab
*Attorney, Agent, or Firm*—Gottlieb, Rackman & Reisman, P.C.

[57] ABSTRACT

An implantable cardioversion defibrillator device is provided with a measuring device for measuring a parameter associated with the defibrillator electrodes such as their impedance and the like. The parameter is measured by applying to the electrodes at regular intervals a series of pulses having a duration shorter than and an amplitude comparable to that of the defibrillation. As a result the patient is unaware of the test pulses. The test pulses may also be used to dump charges from a capacitor in the output stage of the device.

22 Claims, 4 Drawing Sheets

BIPHASIC DEFIBRILLATION WAVEFORM

BIPHASIC DEFRIBILLATION WAVEFORM

HIGH FREQUENCY LEAD TESTING APPARATUS IN AN IMPLANTABLE DEFIBRILLATOR

BACKGROUND OF THE INVENTION

1. Field of Invention

This invention pertains to an implantable cardiac device with means for testing the impedance of its electrodes, and more specifically to a device of this type wherein the electrodes are tested using a high frequency test signal.

2. Description of the Prior Art

Implantable defibrillators are used to provide various types of therapy to a cardiac patient, including, for example defibrillation. These devices consist of a hermetic housing implanted into a patient, and two sets of leads terminating in corresponding electrodes. One set of leads extends from the housing to one or more cardiac chambers. The second set of leads extends from the housing to one or more defibrillator electrodes contacting the myocardia. The housing contains electronic circuitry for monitoring the condition of the patient's heart, usually through the cardiac electrodes. The same set may also be used to provide antibrady- and/or antitachycardia therapy. The second set of electrodes are used to provide defibrillation therapy. The housing further contains a battery which provides power for both signal processing and for the pacing pulses and defibrillation shocks. One such defibrillator is described in U.S. Pat. No. 5,330,504, incorporated herein by reference.

One important parameter for the operation of such a device is the defibrillator electrode impedance. This impedance is indicative of the positioning and integrity of the leads and electrodes. Electrode impedance is also related to the defibrillation threshold. Finally, since successful cardiac defibrillation depends on the amount of energy applied to the cardiac tissue by an electrical shock, and this energy or duration of the shock is also dependent on electrode impedance. Thus, it can be seen that knowing the electrode impedance is important both during implantation, and during normal defibrillator operation.

Typically, until now, electrode impedance in an implanted defibrillator was measured at low voltage and/or current levels to insure that any testing signals used to determine the electrode impedance has no effect on the patient's heart, as disclosed in U.S. Pat. No. 5,215,081, incorporated herein by reference. However, it is believed that such low level testing may not provide an accurate impedance measurement. An alternate testing method is to apply a high voltage shock to the electrodes. However, this shock is painful and uncomfortable to the patient, and potentially dangerous.

OBJECTIVES AND SUMMARY OF THE INVENTION

In view of the above, it is an objective of the present invention to provide a reliable means of testing the impedance of defibrillator electrodes without shocking the patient.

A further objective is to provide an electrode impedance measurement apparatus capable of providing such a measurement with minimal additional circuitry.

A further objective is to provide a device and method which is flexible so that it can be adapted for a variety of testing schemes.

Yet another objective is to provide a defibrillation electrode impedance testing scheme which uses the same components as the defibrillation pulse generator thereby eliminating the need for additional components.

Other objectives and advantages shall become apparent from the following description of the invention.

Briefly, the subject invention pertains to an implantable cardioversion/defibrillation device or ICD, including sensing and pacing electrodes for sensing cardiac activity in a patient, defibrillator electrodes for generating defibrillating pulses when defibrillation therapy is indicated and a pulse controller coupled to these electrodes. The pulse controller includes circuitry for sensing intrinsic cardiac activity in the patient's heart, a signal processor for analyzing these intrinsic signals, and defibrillation pulse generator controlled by the signal processor for generating defibrillation pulses of certain amplitude, phase, duration, and frequency. Importantly, a test pulse generator is provided which is adapted to perform a test on the defibrillator electrodes to determine their impedance. This measurement is used to determine the optimal amplitude and/or duration of the defibrillation pulses, and in addition provides an integrity check for the electrodes. During the measurement stage, high frequency test pulses are applied to the defibrillator electrodes and measurements are made to determine the response to these test pulses from defibrillator electrodes. Preferably, these test pulses are synchronized to ventricular events. Alternatively, the pulses may be used to discharge the high voltage storage capacitor of the defibrillation pulse generator.

DETAILED DESCRIPTION OF THE INVENTION

Figure 1:
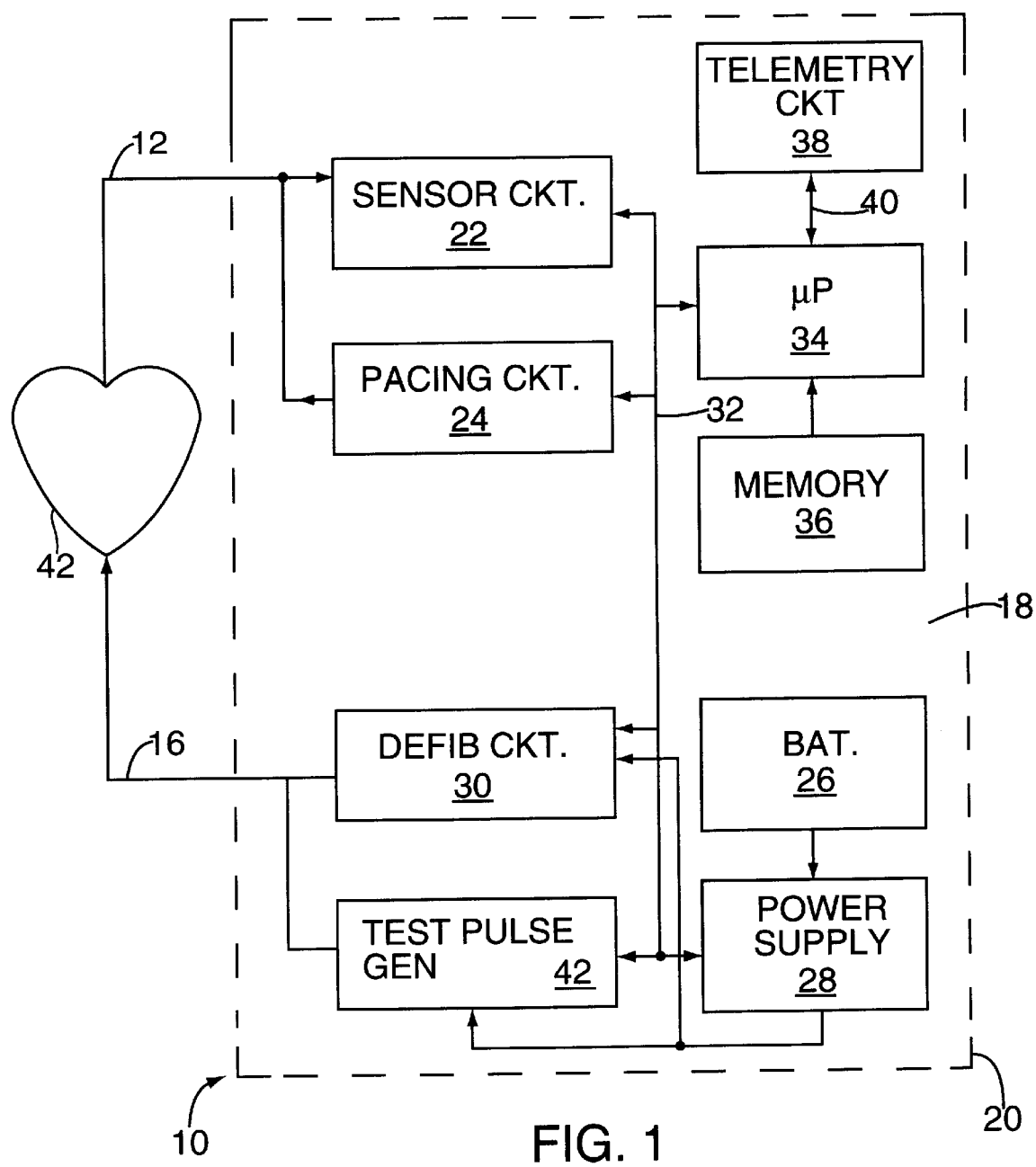
FIG. 1 shows a block diagram of an ICD constructed in accordance with this invention.

Referring first to FIG. 1, an ICD 10 constructed in accordance with this invention includes one set of leads 12 extending to a heart 14. Leads 12 terminate in electrodes (not shown) used for sensing intrinsic cardiac activity as well as pacing. A second set of leads 16 is used to apply defibrillation pulses to the heart 14. The lead sets 12, 16 are connected to a pulse controller 18. The controller 18 includes several electronic circuits enclosed in a hermetic housing 20. Thus, the controller 18 includes a sensor circuit 22 for sensing intrinsic electrical activity from heart 14 via leads 12. The controller 18 may also include a pacing circuit 24 for generating pacing pulses for the heart 14, which pacing pulses may also be delivered via leads 12.

Controller 18 also includes a battery 26 and a power supply 28 for generating power for the various circuits at a voltage generally higher than the voltage of battery 26. Power supply 28 also provides power to defibrillator circuit 30. This circuit 30 provides defibrillation pulses to heart 14 via defibrillator leads 16. Leads 16 terminate in defibrillator electrodes 17 arranged to provide defibrillation therapy. These electrodes 17 may be patches or other types of electrodes well known in the art. The sensor circuit 22, pacing circuit 24, and defibrillator circuit 30 are connected by a bus 32 to a microprocessor 34.

A memory 36 is used to hold programming information for microprocessor 34.

A telemetry circuit 38 communicating with microprocessor 34 via an auxiliary bus 40 allows the microprocessor to exchange information with an external programmer (not shown) and, hence, receive and send information to a clinician.

In one embodiment of the invention, power supply 28 also provides power to a test pulse generator 42. This generator 42 also controlled by microprocessor 34 delivers, test signals to electrode leads 16 as described below.

Figure 2:
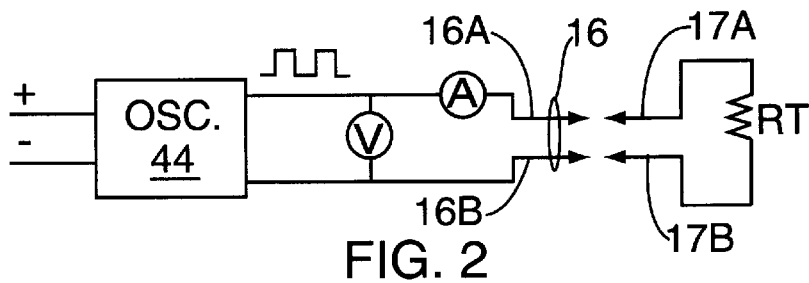
FIG. 2 shows a general schematic diagram of a circuit used for generating test pulses for defibrillator electrodes.

Referring now to FIG. 2, test pulse generator 42 includes a square oscillator 44 receiving power from power supply 28 and in response to commands from the microprocessor 34, it generates waveshapes of a preselected shape such as for example, square waves. Typically these waves can have an amplitude of about 50 volt peak and a frequency of about 100 kHz. The waves are fed to the leads 16A, 16B and electrodes 17A, 17B forming the defibrillator lead set 16. A voltmeter V and an ammeter A are used to monitor the voltage and current fed to the electrodes 17A, 17B, as shown. These parameters are fed to the microprocessor 34 for analysis. The microprocessor 34 uses these parameters to determine the impedance of the electrodes and the cardiac tissue represented in FIG. 2 by resistance RT.

Figure 3:
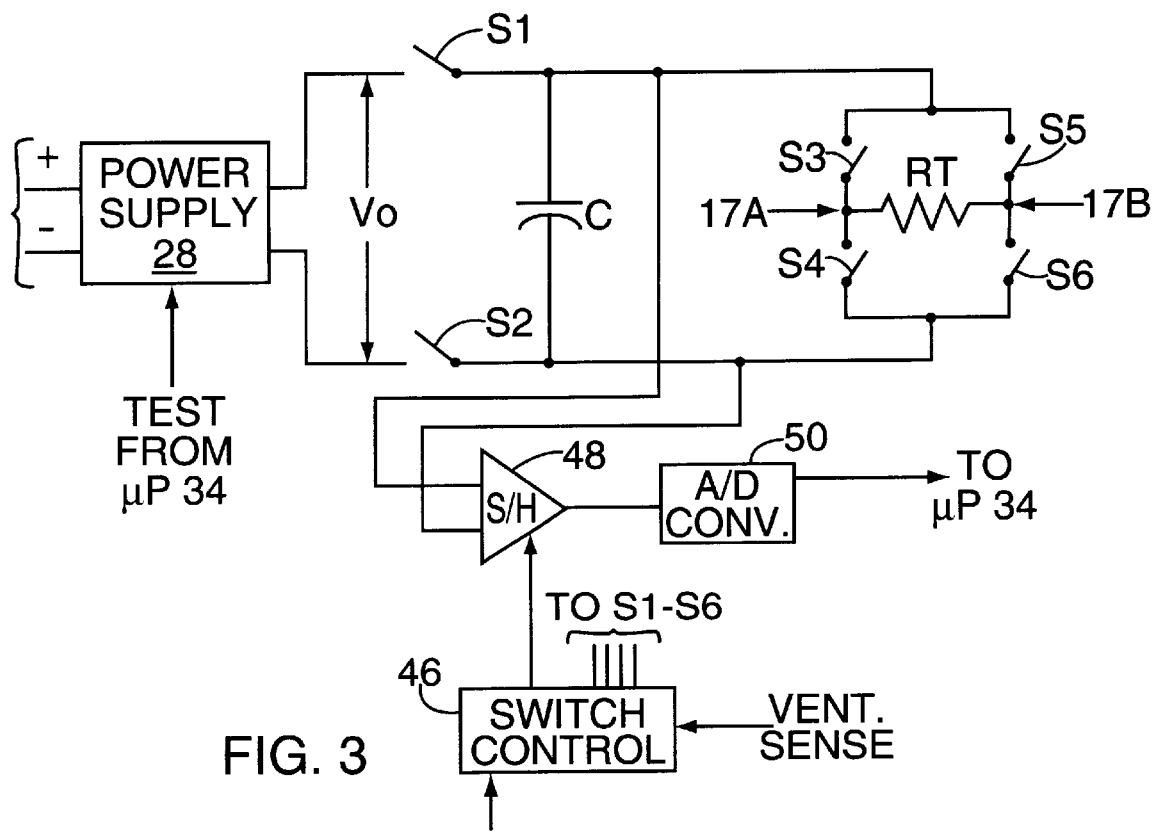
FIG. 3 shows a schematic diagram for a pulse generator used for generating both defibrillator and test signals to the defibrillator electrodes.
Figure 4:
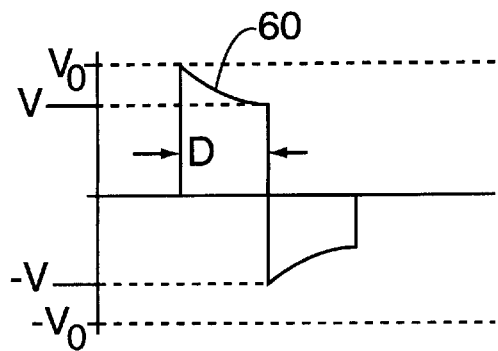
FIG. 4 shows typical defibrillation pulses generated by the circuitry of FIG. 3.

Preferably, the test pulses are generated by the defibrillator circuit 30 itself, rather than by the dedicated test generator 42. Details of the defibrillator circuit 30 are shown in FIG. 3. The circuit 30 has been modified to provide the test pulses as discussed below. As seen in this Figure, circuit 30 comprises a capacitor C and a plurality of electronic switches designated S1–S6. Switches S1 and S2 are selectively closed to charge capacitor C from power supply 28 to a voltage V0. For defibrillation pulses, V0 may have a value of about 50–700 V. Once the capacitor is charged, switches S1 and S2 are open. Switches S3–S6 form a bridge circuit connecting capacitor C to electrodes 17A, 17B. By selectively closing either switches S3, S6 or S4, S5, a set of biphasic defibrillation pulses may be applied to the heart tissues. For example, FIG. 4 shows a set of defibrillation pulses composed of two pulses of opposite polarities. Sets of three pulses of alternate polarities have also been proposed. Details of this type of operation are described more fully in U.S. Pat. Nos. 5,083,562 and 5,215,083, incorporated herein by reference. The switches S1–S6 are opened and closed by a switch control 46. The switch control 46 is responsive to commands from the microprocessor 34. In this manner a defibrillation pulses of alternate polarity are generated, each having a duration D. Note that during defibrillation, each initial pulse of a set, such as pulse 60, shown in FIG. 4 has a peak amplitude V0. In between pulses, the capacitor is recharged to V0 by closing switches S1 and S2.

The sample and hold circuit 50 is activated by switch control 46. It is understood that switch control 46 could be either a separate timer or could be implemented by software on microprocessor 34.

For the purposes of this invention, the defibrillator circuit 30 is constructed to operate as follows. At certain predetermined times, for example, once a month, the microprocessor 34 determines an impedance measurement is required. For this purpose, the power supply 28 is set by a TEST command from the microprocessor (Step 100 in FIG. 6) to produce a test voltage V0 which may be, for example, 50 V.

Next, switches S1 and S2 are closed to charge capacitor C to the preset voltage V0 (Step 102). After the capacitor C is charged, switches S1, S2 are opened (Step 103).

Figure 5A:
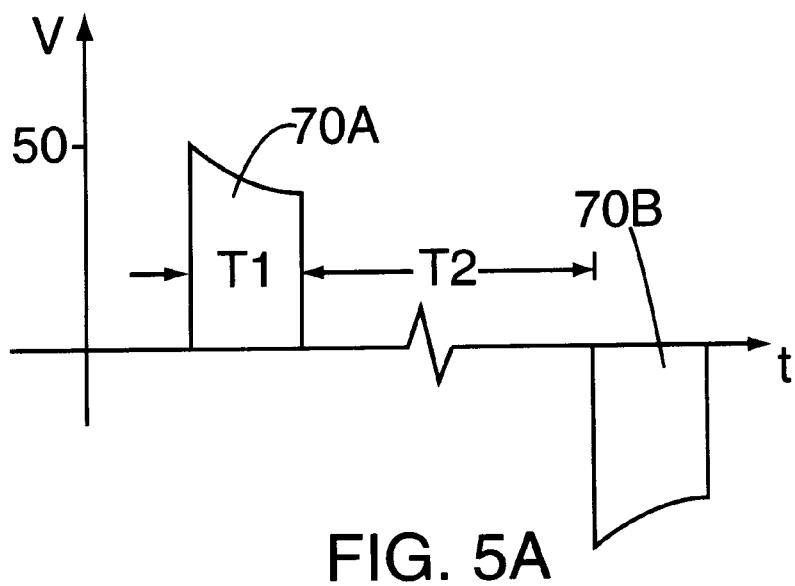
FIG. 5A shows preferred test pulses generated by the defibrillator circuit of FIG. 3.
Figure 5B:
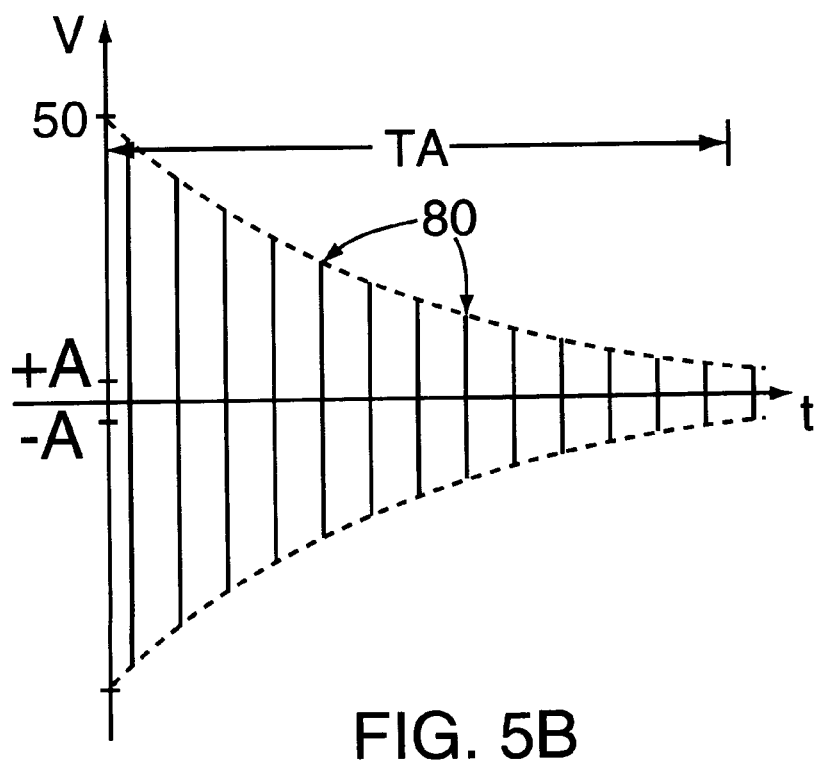
FIG. 5B shows a series of test values obtained from the circuit of FIG. 3.
Figure 6:
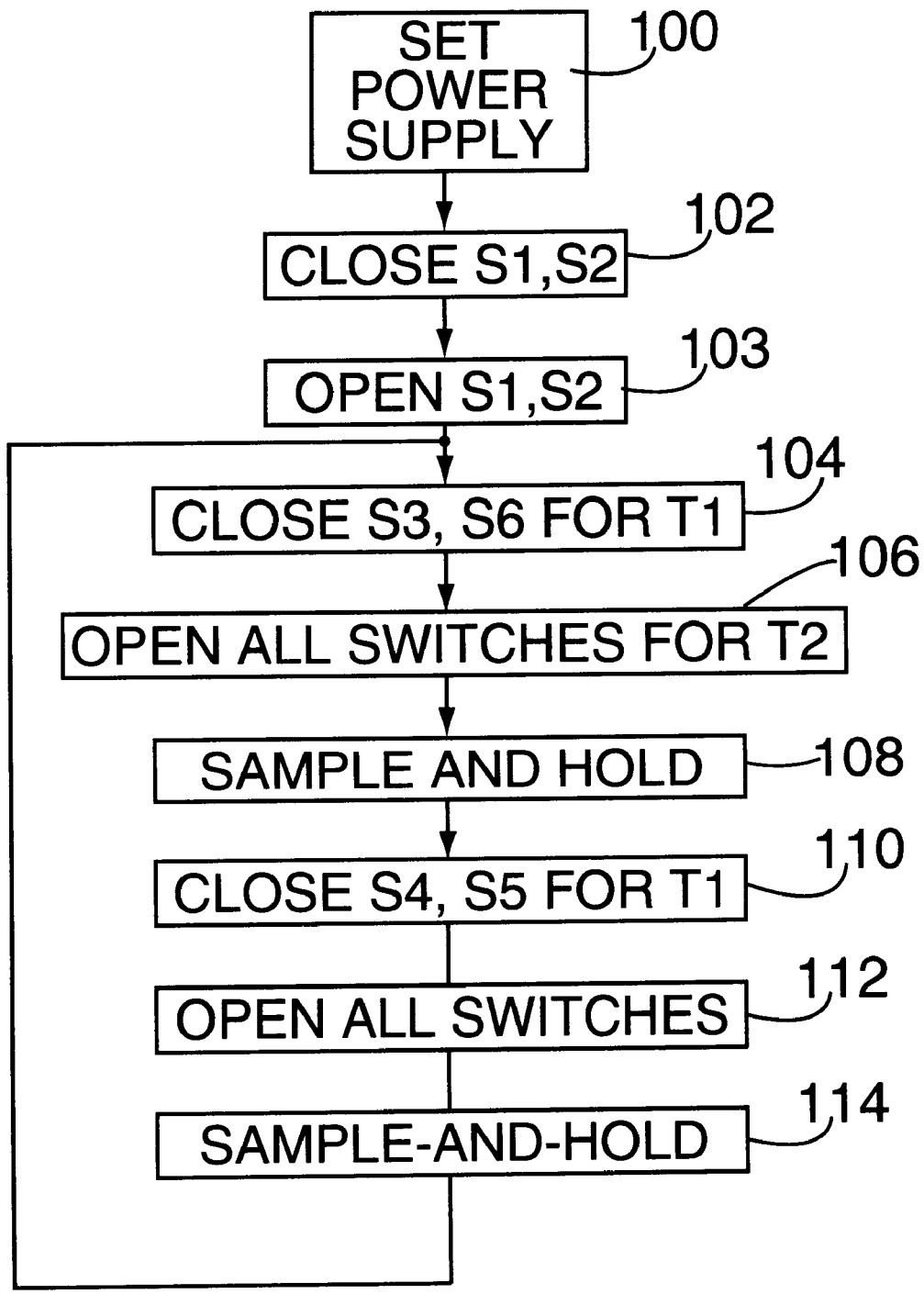
FIG. 6 shows a flow chart for the operation of the ICD of FIGS. 1–3.

A series of test pulses 70 are then produced as described in FIG. 6. The shape of two consecutive pulses 70A, 70B is shown in FIG. 5A. FIG. 5B shows a plurality of test pulses with horizontal time scale being contracted so that pulses appear to be mere vertical lines.

The test pulse 70A start at t0. At this point, in step 104 switches S3 and S6 close allowing capacitor C to start discharging through the tissue impedance RT, thereby producing pulse 70A. After a period T1 the switches are opened (step 106) and the voltage across the capacitor C is sampled by a sample and hold circuit 48 (step 108). The result is converted by D/A converter 50 and provided to microprocessor 34.

All switches remain open for a period To. Next switches S4 and S5 are closed to allow the capacitor to continue discharging (step 110) thereby producing pulse 70B. Importantly, the pulse 70B generated during step 110 has the opposite polarity to the pulse 70A generated during step 104. Moreover, the pulse 70B starts in amplitude where pulse 70A left off since, except for negligible leakage losses, the capacitor C discharges only during period T0.

At the end of period T1, switches S4, S5 are opened (step 112) for a period To and the capacitor C is sampled again (step 114). The microprocessor could determine the electrode impedance by sampling only one or two test pulses, such as 70A, 70B. However, since duration T1 is very short, as discussed below, this calculation may be difficult or inaccurate. A more preferred approach is to apply a large number N of test pulses, with the capacitor C being electrically isolated between the pulses so that it does not get charged between the test pulses. In this way, the voltage across the capacitor droops considerably thereby allowing an accurate determination of the impedance. This sequence of steps 104–114 is repeated N times to obtain a comprehensive number 2N of data points 80. These data points, shown in FIG. 5B, decline exponentially and the microprocessor then performs calculations to determine impedance RT. The information thus derived is used to set the amplitude and/or the duration D of the next set of defibrillation pulses shown in FIG. 4. In addition, if the data points indicate a very rapid decline, i.e. a high rate of decay, a short circuit may be indicated. N may be for example 10.

Importantly, the duration T1 of pulses 70 is selected to be very short as compared to the duration D of defibrillation pulses so that patient feels no discomfort at all during the testing. For example, period T1 may be about 5 microseconds, so that the data points 80 have a frequency of 100 KHz. In contrast, the defibrillation pulse 60 shown in FIG. 4 has an initial maximum amplitude in the range of 700 V, a pulse width or duration D of about 2–6 msec. Thus, while the amplitude of the test pulses is relatively high (in the order of the lowest defibrillation pulses) because their duration and frequency is so much higher, they will be virtually unnoticed by the patient. The alternating test pulses have some additional advantages. First, they have a very small low frequency component thereby resulting in a large current flow without affecting the heart. A similar monophasic test pulse train would have much higher amplitude low frequency component due to the DC offset of the waveform. Therefore the monophasic pulse train would have to have a lower amplitude and would result in a measurement which is much less reliable or require additional circuitry for amplification. Another advantage is that the biphasic test pulse train makes use of, and therefore provides a complete test of the switching network (of switches S1–S6) and hence provides a comprehensive test of this network in addition to the impedance measurement previously discussed.

An important consideration in testing the electrodes is the total duration of the test. This parameter may be controlled in a number of ways. One way is to monitor the absolute peak amplitudes of successive test waveshapes 70A. The time TA required for these waveshapes to drop below a threshold value A is then indicative of the decay rate, and therefore the electrode impedance.

A second way is to set the number of test waveshapes to a preset number, such as for example 25 or 50. The total drop in the peak amplitude of the last test waveshape together with the time for the test is indicative again of the impedance.

Another consideration is the timing of and separation between each test waveshape 70A. As previously stated, the initial amplitude of the waveshapes is close to the lowest fibrillation pulses. To insure that the test does not induce fibrillation, the test waveshapes are preferably synchronized that they triggered right after the sensing of a ventricular event be sensor circuit 22.

One function of the test pulses and circuitry described above is to determine the defibrillation electrode impedance. However, the same circuitry and pulses may also be used for charge dumping. More specifically, the test pulses may be used to discharge capacitor C without damaging the patient's tissues.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable defibrillation device comprising:
   a generator device for generating defibrillation pulses of a first duration and having amplitudes within a preselected defibrillation range and test pulses of a second duration, at least one of said test pulses having a test amplitude within said preselected defibrillation range;
   defibrillation electrodes for delivering said defibrillation pulses and said test pulses to a patient's heart; and
   a measuring device for measuring a parameter related to said defibrillation electrodes, said measuring device including a sensor for sensing said parameter in response to said one of said test pulses, wherein said second duration is shorter than said first duration and is selected to insure that said test pulses has no adverse effect on said patient.

2. The device of claim 1 wherein said generator device includes a first pulse generator for generating said defibrillation pulses and a second pulse generator for generating said test pulses.

3. The device of claim 1 wherein said generator device includes a power supply, a plurality of switches coupled to said power supply and a switch controller for switching said switches at a first rate to generate said defibrillation pulses and in at a second rate to generate said test pulses.

4. The device of claim 1 wherein said defibrillation pulses have a peak defibrillation amplitude and said test amplitude is lower than said peak defibrillation amplitude.

5. An implantable cardiac defibrillation device comprising:
   a controller generating a defibrillation command and a test command;
   defibrillation electrodes;
   a defibrillation generator for generating defibrillation pulses in response to said defibrillation command and test pulses in response to said test command, said defibrillation and test pulses being applied to said defibrillation electrodes, said defibrillation pulses having amplitudes within a preselected defibrillation range, and at least one of said test pulses having a test pulse amplitude within said preselected defibrillation range; and
   a measuring device for generating a parameter responsive to said test pulses;
   wherein said test pulses have a test pulse duration shorter than said defibrillation pulses, said test pulse duration being selected to prevent adverse effects to said heart.

6. The device of claim 5 wherein said defibrillator generator includes a defibrillator pulse generator for generating said defibrillation pulses and a test pulse generator for generating said test pulses.

7. The device of claim 5 wherein said defibrillator generator includes a power source, an electronic switch arrangement coupled to said power source and a switch controller for operating said switch arrangement to generate said defibrillator and test pulses.

8. The device of claim 7 wherein said defibrillator generator further comprises an energy storage device.

9. The device of claim 8 wherein said energy storage device is a capacitor.

10. The device of claim 5 wherein said defibrillation pulses have a peak defibrillation pulse amplitude and wherein said test pulse amplitude of said one of said test pulses is smaller than said peak amplitude.

11. The device of claim 5 wherein said test pulses and said defibrillation pulses are biphasic pulses.

12. The device of claim 5 wherein said preselected defibrillation range is between 50 and 700 V.

13. The device of claim 12 wherein said defibrillation pulses have a defibrillation pulse duration of about 2–6 msec and said test pulse duration is about 5 microseconds.

14. The device of claim 5 wherein each said test pulses have amplitudes decreasing sequentially in accordance with an exponential decay and wherein said measuring device is arranged to determine said parameter from said exponential decay.

15. An implantable defibrillation device comprising:
   a pair of defibrillation electrodes;
   controller means for generating a defibrillation command and a test command;
   pulse generator means connected to said defibrillation electrodes and responsive to said defibrillation command for generating defibrillation pulses having a defibrillation amplitude in a preselected range; said pulse generator means further being responsive to said test command for generating test pulses having test pulse amplitudes, the test pulse amplitude of at least an initial test pulse of said test pulses being within said preselected range; and
   impedance determinator means for determining an impedance between said defibrillation electrodes by analyzing said test pulses.

16. The device of claim 15 wherein said pulse generator means includes:

a power source;

capacitor means;

switch means coupled to said power source and said capacitor means and arranged to open and close in response to said defibrillation and said test commands, said switch means being arranged to connect said capacitor to said power source to charge said capacitor means to a capacitor voltage within said preselected defibrillation range and to disconnect said capacitor means from said power source while said test pulses are generated.

17. The device of claim 16 wherein said switch means is further responsive to said defibrillation and test commands to selectively connect said capacitor means to said electrodes to apply said defibrillation and said test pulses.

18. The device of claim 17 wherein said capacitor voltage decays while said test pulses are applied to said electrodes resulting in a corresponding decay in the amplitudes of successive test pulses, said impedance detector means being arranged to analyze said decay to detect said impedance.

19. The device of claim 16 wherein said preselected range comprises 50–700 V.

20. In an implantable defibrillator capable of applying defibrillation pulses through a pair of defibrillation electrodes to a patient's heart, said defibrillation pulses each having a defibrillation pulse duration and an amplitude within a preselected range, a method of determining the impedance between said pair of electrodes after implantation, said method comprising:

applying a plurality of test pulses to said defibrillation electrodes, said test pulses having a test pulse duration and a test pulse amplitude, wherein at least one of said test pulses has a test pulse amplitude within said preselected range, and said test pulse duration is selected to be shorter than said defibrillation pulse duration to prevent adverse effects to the heart; and measuring a characteristic of said test pulses.

21. The method of claim 20 wherein said implantable defibrillation device includes a capacitor and a power supply selectively connected to said capacitor to charge said capacitor to a voltage within said preselected range, and wherein said step of applying a plurality of test pulses includes disconnecting said capacitor from said power supply while said plurality of test pulses are generated and selectively connecting said capacitor to said defibrillation electrodes to discharge said capacitor through said defibrillation electrodes to cause the amplitudes of said test pulses to decay.

22. The method of claim 21 wherein said step of measuring comprises analyzing said decay.

* * * * *